US009198879B2

(12) United States Patent
Chaturvedi

(10) Patent No.: US 9,198,879 B2
(45) Date of Patent: Dec. 1, 2015

(54) PHARMACOLOGICALLY OPTIMIZED MULTIMODAL DRUG DELIVERY SYSTEM FOR NORDIHYDROGUIARETIC ACID (NDGA)

(71) Applicant: Napo Pharmaceuticals, Inc., San Francisco, CA (US)

(72) Inventor: Pravin R. Chaturvedi, Andover, MA (US)

(73) Assignee: NAPO PHARMACEUTICALS, INC., San Francisco, CA (US)

( * ) Notice: Subject to any disclaimer, the term of this patent is extended or adjusted under 35 U.S.C. 154(b) by 0 days.

(21) Appl. No.: 13/911,893

(22) Filed: Jun. 6, 2013

(65) Prior Publication Data

US 2013/0274346 A1    Oct. 17, 2013

Related U.S. Application Data

(62) Division of application No. 13/453,618, filed on Apr. 23, 2012.

(60) Provisional application No. 61/478,246, filed on Apr. 22, 2011.

(51) Int. Cl.
*A61K 31/00* (2006.01)
*A61K 31/05* (2006.01)
*A61K 9/00* (2006.01)

(52) U.S. Cl.
CPC .............. *A61K 31/05* (2013.01); *A61K 9/0053* (2013.01)

(58) Field of Classification Search
USPC ........................................................ 514/734
See application file for complete search history.

(56) References Cited

U.S. PATENT DOCUMENTS

| | | | | |
|---|---|---|---|---|
| 3,934,034 | A * | 1/1976 | Manning | ........................ 514/734 |
| 5,262,173 | A | 11/1993 | Sheth et al. | |
| 5,827,898 | A | 10/1998 | Khandwala | |
| 2007/0149466 | A1 | 6/2007 | Milburn et al. | |
| 2007/0166370 | A1 | 7/2007 | Odidi | |
| 2009/0280112 | A1 | 11/2009 | Goldfine et al. | |
| 2009/0306070 | A1 | 12/2009 | Heller et al. | |
| 2010/0022528 | A1 | 1/2010 | Chen et al. | |
| 2010/0255087 | A1 | 10/2010 | Coulter | |

OTHER PUBLICATIONS

Waller, et al, A Phytochemical Investigation of *Larrea divaricata* Cav., J. Amer. Pharm. Assoc. Sci., vol. 34, pp. 78-81 (1945).
Winkelman, Frequently Used Medicinal Plants in Baja California Norte, J. Ethnopharm.18:109-131 (1986).
Gowri, M. S. et al., Effect of Masoprocol on Glucose Transport and Lipolysis by Isolated Rat Adipocytes, Metabolism: Clinical and Experimental, 48(4): 411-414 (1999).
Hwu et al., New nordihydroguaiaretic acid derivatives as anti-HIV agents, Bioorganic and Medical Chemistry Letters 18, pp. 1884-1888 (2008).
Chen, Q., Nordihydroguaiaretic Acid Analogues: Their Chemical Synthesis and Biological Activities, Current Topics in Medicinal Chemistry, 9:1636-1659 (2009).
Kortejarvi et al., Level A In Vitro-In Vivo Correlation (IVIVC) Model with Bayesian Approach to Formulation Series, J. Pharm. Sci. 95 (7), pp. 1595-1605 (2006).
Wang et al., In Vitro Dissolution and In Vivo Oral Absorption of Methylphenidate from a Bimodal Release Formulation in Healthy Volunteers, Biopharmaceutics & Drug Disposition 25: 91-8 (2004).
Amidon et al., A Theoretical Basis for a Biopharmaceutic Drug Classification: The Correlation of in Vitro Drug Product Dissolution and in Vivo Bioavailability, Pharmaceutical Research 12(3): 413-420 (1995).
Streubel et al., Bimodal drug release achieved with multi-layer matrix tablets: transport mechanisms and device design, Journal of Controlled Release, vol. 69, pp. 455-468 (2000).
Abdul et al., A flexible technology for modified release of drugs: multi layered tablets, Journal of Controlled Release, vol. 97, pp. 393-405 (2004).
Efentakis et al., Comparative evaluation of various structures in polymer controlled drug delivery systems and the effect of their morphology and characteristics on drug release, Eur Polymer J, vol. 42, pp. 1183-1195 (2006).
Zelikin et al., Disulfide Cross-Linked Polymer Capsules: En Route to Biodeconstructible Systems, Biomacromolecules, vol. 7, pp. 27-30 (2006).
Macleod et al., The potential use of mixed films of pectin, chitosan and HPMC for bimodal drug release, Journal of Controlled Release, vol. 58, pp. 303-310 (1999).
Nagarsenker et al., Preparation and evaluation of liposomal formulations of tropicamide for ocular delivery, Int. J. Pharm., vol. 190, pp. 63-71 (1999).
Tho et al., Extrusion/Spheronization of Pectin-Based Formulations. I. Screening of Important Factors, AAPS PharmSciTech, vol. 2(4), pp. 54-62 (Dec. 1, 2001).
Atyabi et al., In vitro evaluation and modification of pectinate gel beads containing trimethyl chitosan, as a multi-particulate system for delivery of water-soluble macromolecules to colon, Carbohydrate Polymers, vol. 61, pp. 39-51 (2005).
Lakshmi et al., Biodegradable polyphosphazenes for drug delivery applications, Adv. Drug Delivery Rev., vol. 55, pp. 467-482 (2003).
Moussy et al., Transport Characteristics of a Novel Local Drug Delivery System Using Nordihydroguaiaretic Acid (NDGA)-Polymerized Collagen Fibers, Biotechnol. Prog., vol. 23, pp. 990-994 (2007).
Franco et al., Eicosanoid and gastroprotection by copper derivatives and NDGA, Inflamm. Res., vol. 44, pp. 139-142 (1995).
Zakharian et al., A Fullerene-Paclitaxel Chemotherapeutic: Synthesis, Characterization, and Study of Biological Activity in Tissue Culture, J. Am. Chem. Soc., vol. 127, pp. 12508-12509 (2005).

(Continued)

*Primary Examiner* — Michael G Hartley
*Assistant Examiner* — Robert Cabral
(74) *Attorney, Agent, or Firm* — Troutman Sanders, LLP

(57) ABSTRACT

The present invention relates generally to compositions and methods for oral delivery of nordihydroguaiaretic acid (NDGA). More particularly, the present invention relates to pharmacologically optimized multimodal drug delivery systems for orally administered NDGA and methods for preparation and use thereof.

16 Claims, 8 Drawing Sheets

(56) References Cited

OTHER PUBLICATIONS

Youngren et al., Nordihydroguaiaretic acid (NDGA) inhibits the IGF-1 and c-rbB2/HER2/neu receptors and suppresses growth in breast cancer cellsBreast Cancer Res. Treat., vol. 94, pp. 37-46 (2005).

Mandal et al., Design and development of microemulsion drug delivery system of atorvastatin and study its intestinal permeability in rats, International Journal of Drug Delivery, vol. 2, pp. 69-75 (2010).

Tansey et al., Synthesis and characterization of branched poly (L-glutamic acid) as a bidegradable drug carrier, Journal of Contorlled Release, vol. 94, pp. 39-51 (2004).

Shah, AC, et al., "Gel-matrix systems exhibiting bimodal controlled release for oral drug delivery," Journal of Controlled Release (1989), vol. 9, pp. 169-175; Elsevier Science Publishers B.V., Amsterdam.

Communication from European Patent Office with Extended European Search Report and Written Opinion, mailed Sep. 29, 2014 for EP12773908.4.

* cited by examiner

PHARMACOLOGICALLY OPTIMIZED MULTIMODAL DRUG DELIVERY SYSTEM FOR NORDIHYDROGUIARETIC ACID (NDGA)

CROSS-REFERENCE TO RELATED APPLICATIONS

This application is a divisional application of U.S. application Ser. No. 13/453,618 filed Apr. 23, 2012, which claims priority benefit of U.S. provisional patent application Ser. No. 61/478,246 filed Apr. 22, 2011, which is incorporated by reference in its entirety.

TECHNICAL FIELD

The present invention relates generally to compositions and methods for oral delivery of nordihydroguaiaretic acid (NDGA). More particularly, the present invention relates to pharmacologically optimized multimodal drug delivery systems for orally administered NDGA and methods for preparation and use thereof

BACKGROUND OF THE INVENTION

Hyperglycemia, hypertriglyceridemia and hyperinsulinemia are key clinical features of patients presenting with metabolic disorders and/or non-insulin-dependent diabetes mellitus (NIDDM). Following maximal insulin secretion by the pancreas to regulate rising glucose and triglyceride levels, higher glucose and triglyceride levels cannot be regulated by the circulating high levels of insulin, resulting in "insulin resistance" in patients with diabetes and metabolic disorders. In pre-diabetic conditions, patients have moderate levels of hyperglycemia and hypertriglyceridemia associated with moderate hyperinsulinemia. If there are better therapeutic agents available to regulate glucose and triglyceride levels when the patients do not have advanced disease, there will be a big therapeutic and pharmacoeconomic benefit from management of such patients before they become "insulin resistant".

Nordihydroguiaretic Acid ("NDGA") is a bisphenolic compound that occurs naturally in the leaves and small stems of the creosote bush, Larrea divaricata. It was first isolated by Walter, et al., in 1945 (J. Amer. Pharm. Assoc. Sci., 34:78-81.) Its use in traditional medicine was widespread in the 20$^{th}$ century, and included the treatment of diabetes, kidney problems, urinary tract infections, rheumatism, arthritis, wounds, skin injuries and paralysis (Winkelman, et al., J. Ethnophann. 18:109-131 (1986).)

NDGA has been shown to enhance glucose disposition and inhibit lipolysis (Gowri, M. S. et al., Metabolism: Clinical and Experimental, 48(4): 411-414 (1999).) As demonstrated using isolated rat adipocytes, NDGA has a profound effect on glucose and lipid metabolism at the cellular level, which involves at least in part its ability to optimize insulin sensitivity of glucose and lipids.

Effective oral delivery of small molecule therapeutic agents is complicated by the insolubility of the agent. Like many other phenolic small molecule therapeutics, NDGA is insoluble in aqueous media, but is soluble in organic solvents such as methanol and ethanol. Attempts have been made to increase its solubility in water by derivatizing the molecule. For example, U.S. Patent Application No. 2009/0306070 describes a tetra-O-substituted butane bridge modified form of NDGA with enhanced water solubility. In U.S. Patent Application 2010/0022528, solubility is enhanced by forming tetra-substituted NDGA derivatives vie ether bonds and/or carbamate bonds. Another approach is described in Bioorganic and Medical Chemistry Letters, 18(6):1884-1888 (2008), wherein NDGA is derivatized into its corresponding phenol ether, carbamate or carbonate.

Although the use of a more water soluble form of NDGA for oral delivery may enhance absorption overall, this approach alone does not address the problems associated with attempts to enhance efficacy by tailoring absorption kinetics and physiological delivery profiles for specific purposes. More specifically, "immediate" release formulations of NDGA will not allow optimal pharmacokinetic profiles of NDGA to provide adequate regulation of increased glucose and triglyceride levels.

Accordingly, there is a need to enhance efficacy of orally administered NDGA formulations to optimize absorption kinetics, slowing elimination, improving physiological delivery profiles, reducing total NDGA dose levels and dosing frequency, and overall better therapeutic management of hyperglycemia and hypertriglyceridemia which is observed in patients with early as well as advanced stages of diabetes and/or metabolic disorders. As described herein, such formulations involve the use of multimodal release dosage forms of NDGA. Examples of such formulations include bimodal oral release dosage forms, which incorporate slow- and sustained-release oral dose delivery systems, to allow pharmacologically optimal oral delivery of NDGA.

SUMMARY OF THE INVENTION

The present invention relates generally to compositions and methods for oral delivery of nordihydroguaiaretic acid (NDGA). More particularly, the present invention relates to pharmacologically optimized multimodal drug delivery systems for orally administered NDGA and methods for preparation and use thereof.

Accordingly, in one embodiment, the present invention is an orally administered multimodal drug delivery system for nordihydroguiaretic acid (NDGA), that includes a first portion of NDGA that is released in the stomach (i.e. its peak release occurs at stomach pH); and a second portion of NDGA that is released in the small intestines, such that at least 90% of the NDGA is absorbed before reaching the large intestines, and wherein the NDGA absorption exhibits multimodal delivery kinetics. It should be understood that the exact form and thus the chemical release properties of the first and second portion of NDGA may be the same or different. In addition, either or both the first and second portions of NDGA may be the compound depicted in FIG. 1.

Accordingly such a drug delivery system may exhibit a peak pH release of the first NDGA portion at a pH of between 1.0 and 4.0, and a peak pH release of the second NDGA portion at a pH of between 5.0 and 7.5. In addition, at least 90% of the first and second portion of NDGA may be released at a pH below 8.0.

For example, the second portion of the NDGA may be released in the duodenum, the jejunum and/or the ileum.

In one embodiment, the drug delivery system may be a tablet having an outer portion and an inner portion, wherein the first portion of NDGA is in the outer portion and the second portion of NDGA is in the inner portion. In such a delivery system, the outer portion may have a peak release at a pH of 4.0 or less, and the inner portion may have a peak release at a pH of 5.0 or greater.

In another embodiment, the drug delivery system may have the first portion of NDGA is in a first bead, wherein the NDGA is released from the first bead at a peak pH of 4.0 or less, and wherein the second portion of NDGA is in a second bead, wherein the NDGA is released from the second bead at a peak pH of 5.0 or greater.

In yet another embodiment, the drug delivery system may be a heterogeneous biodegradable matrix, wherein the first portion of NDGA is incorporated within a first portion of the biodegradable matrix having a peak release at a pH of 4.0 or less, and a second portion of the biodegradable matrix having a peak release at a pH of 5.0 or greater.

Alternatively, the drug delivery system may consist of a homogeneous vehicle, with two different forms of NDGA, the first portion of which has a first solubility in water, and the second portion of which has a second solubility in water, wherein the first solubility is at least 10% greater or less than the second solubility. In another embodiment, the solubility of the second portion may be 20% greater or less than, 30% greater or less than, or even 50% greater or less than the first portion.

The drug delivery systems of the present invention are useful to treat all disease states that are known to respond to NDGA, such as diabetes, including non-insulin dependent diabetes mellitus (NIDDM), cancer, metabolic disorders, etc. The metabolic disorder may manifest as any or all of the following: high free fatty acids, hyperlipidemia, hyperglycemia, hypertriglyceridemia and/or hyperinsulinemia Any disease state associated with high glucose and/or high triglycerides is expected to be treatable with the drug delivery systems of the present invention.

The drug delivery systems of the present invention may be prepared by providing a first portion of NDGA in a first form or vehicle that is released at a peak pH of between 1 and 4; and providing a second portion of NDGA in a second form or vehicle that is released at a peak pH of between 5 and 7.5; wherein at least 90% of the NDGA in the drug delivery system is released at a pH of below 8.0.

Other aspects of the invention are found throughout the specification.

DETAILED DESCRIPTION OF THE INVENTION

Figure 1:
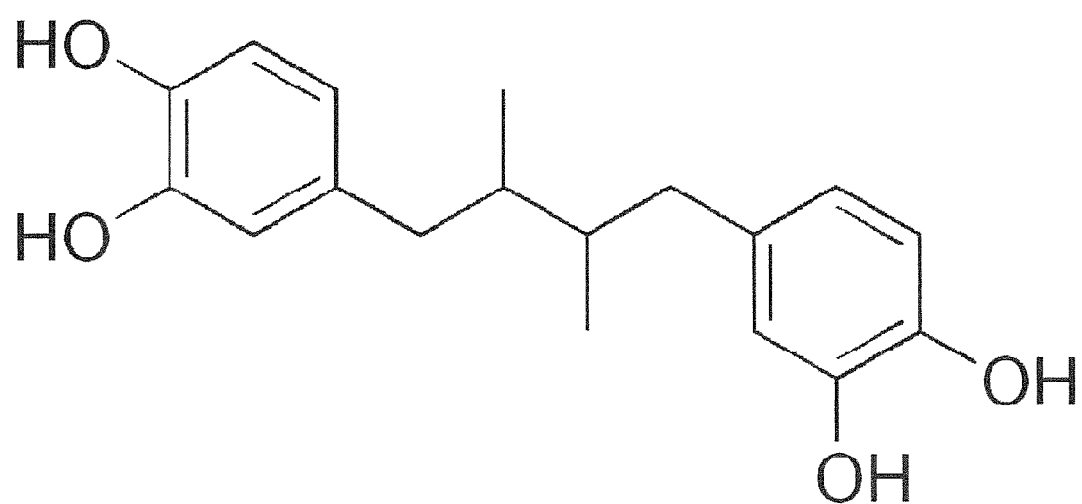
FIG. 1 is a depiction of the structure of NDGA.

The present invention relates generally to compositions and methods for delivering NDGA. More particularly, the present invention relates to pharmacologically optimized multimodal drug delivery systems for orally administered NDGA and methods for preparation thereof.

In the description that follows, a number of terms used in the field of molecular biology, immunology and medicine are extensively utilized. The following non-limiting definitions provide a clear and consistent understanding of the specification and claims, including the scope to be given such terms.

When the terms "one," "a," or "an" are used in this disclosure, they mean "at least one" or "one or more," unless otherwise indicated.

The term "subject" as used herein refers to an animal, including, but limited to, an ovine, bovine, ruminant, lagomorph, porcine, equine, canine, feline, rodent or primate, e.g. a human. Typically, the terms "subject" and "patient" are used interchangeably herein in reference, for example, to a mammalian subject, particularly a human subject.

NDGA

NDGA is a compound isolated from Larrea tridentate, which is more commonly known as the creosote bush. Although as used in the scientific literature, the term "NDGA" usually refers to the structure depicted in FIG. 1, it should be understood that, unless otherwise indicated, the term "NDGA is used to refer to a class of dicatecholic compounds according to Formula I, which are all collectively referred to herein as NDGA:

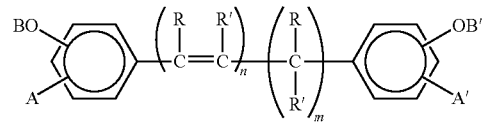

The term "form of NDGA" is meant to refer to the compound according to Figure I, and any derivatives/analogues of Formula I as described below. It will be apparent to anyone of skill in the art that the different pharmacological properties, release kinetics and absorption characteristics of any such forms of NDGA can easily be characterized using routine experimentation as taught herein and elsewhere.

In Formula I, R and R' are independently H or a $C_1$-$C_{20}$ alkyl or a $C_2$-$C_{20}$ alkenyl group which may be branched or unbranched. In a preferred embodiment R and R' are independently H or a $C_1$-$C_{10}$ alkyl, more preferably a $C_1$-$C_6$ alkyl, or a $C_2$-$C_{10}$ alkenyl, more preferably a $C_2$-$C_8$ alkenyl, which may be substituted or not substituted. Alternatively, R and R' are such that together a cycloalkyl or cycloalkenyl ring is formed. Each of (C(R)=C(R')) and/or (C(R)(R')) may be the same or different. A and A' are independently a $C_2$-$C_{20}$ alkanoyl, preferably $C_2$-$C_{10}$ alkanoyl, more preferably $C_2$-$C_6$ alkanoyl; acylamino, preferably $C_2$-$C_{10}$ acylamino, more preferably $C_2$-$C_6$ acylamino; $C_2$-$C_{20}$ acyloxy, preferably $C_2$-$C_{10}$ acyloxy, more preferably $C_2$-$C_6$ acyloxy; $C_1$-$C_{20}$ alkoxy, preferably $C_1$-$C_{10}$ alkoxy, more preferably $C_1$-$C_6$ alkoxy; $C_2$-$C_{20}$ alkoxycarbonyl, preferably $C_2$-$C_{10}$ alkoxycarbonyl, more preferably $C_2$-$C_6$ alkoxycarbonyl; $C_1$-$C_{20}$ alkyl amino, preferably $C_1$-$C_{10}$ alkyl amino, more preferably $C_1$-$C_6$ alkyl amino; $C_2$-$C_{20}$ alkylcarboxyl, preferably $C_2$-$C_{10}$ alkylcarboxyl, more preferably $C_2$-$C_6$ alkylcarboxyl, amino, $C_2$-$C_{20}$ carbalkoxyl, preferably $C_2$-$C_{10}$ carbalkoxyl, more preferably $C_2$-$C_6$ carbalkoxyl, carboxyl, cyano, halo, or hydroxy. The substituents on the phenolic oxygen B and B' are independently H, $C_2$-$C_{20}$ alkanoyl, $C_3$-$C_{20}$ alkenoyl, $C_2$-$C_2$-$C_{20}$ alkenyl, $C_2$-$C_{20}$ alkoxycarbonyl, $C_1$-$C_{20}$ alkyl, aroyl, aralkanoyl, $C_2$-$C_{20}$ carbamoyl, or phosphate. In a preferred embodiment, B and B' are independently H, a $C_2$-$C_{10}$ alkanoyl, more preferably $C_2$-$C_6$ alkanoyl; a $C_3$-$C_{10}$ alkenoyl, more preferably $C_3$-$C_6$ alkenoyl; a $C_2$-$C_{10}$ alkenyl, more preferably $C_2$-$C_6$ alkenyl; a $C_2$-$C_{10}$ alkoxycarbonyl, more preferably $C_2$-$C_6$ alkoxycarbonyl; $C_1$-$C_{10}$ alkyl, more preferably a $C_1$-$C_6$ alkyl, a $C_2$-$C_{10}$ carbamoyl, more preferably a $C_2$-$C_6$ carbamoyl, or phosphate. When both A and A' are alkoxy, at least one of B and B' is H.

In Formula I, n and m are independently equal to 0 to 6. In one embodiment, in Formula I, B and B' are hydrogen and A and A' are independently hydroxyl or $C_2$-$C_{20}$ acyloxy. Alternatively, B and B' are hydrogen and A and A' are hydroxyl.

In another embodiment of Formula I, n is 0 and m is 2 to 4 and each of R and R' is independently hydrogen or $C_1$-$C_{20}$ alkyl, or a $C_1$-$C_{10}$ alkyl or a $C_1$-$C_6$ alkyl. In a preferred embodiment of the method in the compounds, B and B' are hydrogen; A and A' are independently hydroxyl or $C_1$-$C_{20}$ acyloxy; n is 0; m is 2 to 4; and R and R' are independently hydrogen or $C_1$-$C_{20}$ alkyl or a $C_1$-$C_{10}$ alkyl, or a $C_1$-$C_6$ alkyl.

In one embodiment, the NDGA according to Formula I is meso, d-, l- or dl-4,4'-(2,3-dimethyl-1,4-butanediol)bis[1,2-benzenediol], and is depicted in FIG. 1.

The NDGAs according to the present invention include, without limitation, compounds according to Formula I, geometric or optical isomers thereof, and/or pharmaceutically acceptable salts thereof. Suitable pharmaceutically acceptable salts according to the present invention include but are not limited to hydrochloride, hydrobromide, phosphate, sulfate, acetate, succinate, ascorbate, tartrate, gluconate, benzoate, malate, and fumarate.

NDGA Release Kinetics a. Solubility

NDGA is a poorly water-soluble drug, as are most drugs that exert their pharmacological action at or in biological membranes or on membrane-associated proteins. Many such drugs also tend to be weakly acidic. This poses challenges for orally administered forms of the drug. Examples of such drugs are azeclofenac, naproxen, celecoxib, buprenorphine, meloxicam, levothyroxine, paclitaxel, methylphenidate, griseofulvin, carbamazepine, medroxyprogesterone acetate, glipizide and fenofibrate. Derivatized forms of NDGA with increased solubility are known. See, for example, Chen, Q., Current topics in Medicinal Chemistry, 9:1636-1659 (2009).

b. Absorption and Release

As discussed above, it has been discovered that the most useful form of delivery of NDGA is one that addresses hyperglycemia, hypertriglyceridemia and hyperinsulinemia in patients that present with metabolic disorders and/or non-insulin-dependent diabetes mellitus (NIDDM). As such, efficacy can be enhanced by targeting delivery in a multimodal and sustained manner across multiple locations along the intestinal tract. A single change in solubility alone will not achieve this enhancement. In addition, if prolonged delivery or a complex modified or sustained release pharmacokinetic profile is desired, enhancing solubility alone may result in hastened (immediate) delivery, which will not be appropriate for the purposes of treatment of patients that have hyperglycemia and hypertriglyceridemia.

Furthermore, complex modification of oral delivery profiles of NDGA will allow controlling the elimination rate of NDGA, given that NDGA has a rapid elimination profile and short half-life, when administered as an immediate release dosage form, such as an oral syrup or an oral capsule. By preparing modified release dosage forms, one can control the rapid elimination of NDGA and provide a more convenient dosing regimen, such as one or two daily doses, while providing an optimal pharmacokinetic profile to regulate glucose and triglyceride levels.

An additional benefit of a multimodal release profile of NDGA is the "dose-sparing" effect compared to administration of an immediate release dosage form. Such a benefit is obtained through controlling the elimination rate of NDGA by utilizing a complex multimodal release dosage form, which prevents the need for administration of an immediate release dosage form multiple times during the day. Thus, in an ideal situation, the dosage forms described herein allow the administration of an oral formulation of NDGA no more than once (q.d.) or twice (b.i.d) daily, which allows for better patient compliance, lesser requirements for total daily doses (dose-sparing benefit), as well as better regulation of glucose and triglyceride levels in patients with diabetes and/or metabolic disorders.

The term "multimodal" as used herein refers to the concentration curves over time that are measured after oral administration of the delivery system. Such curves are "multimodal" if they exhibit anything other than a normal distribution curve that is essentially symmetrical at its maximum. A normal distribution curve may be positively or negatively skewed, but it is still nonetheless a unimodal curve. See FIGS. 4 to 8 for exemplary unimodal curves that are positively skewed, i.e. the concentration levels trail off after reaching their maximum at a slower rate than the rate at which the maximum was reached. Since plasma concentration following oral administration is a function of absorption, the absorption kinetics of an oral NDGA delivery system are considered "multimodal" if the concentration vs. time curves exhibit a multimodal distribution pattern.

In addition to exhibiting multimodal absorption, the delivery systems of the present invention also exhibit at least two different pH-dependent release maxima. Indeed, it is a goal of the delivery systems of the present invention to release at least a portion of the NDGA to both the stomach and the small intestines so that they may be absorbed at both locations, but for essentially all of the NDGA to be released and thereafter absorbed before reaching the large intestines. This differential delivery is discussed in greater detail elsewhere herein.

As used herein, the pH-dependent "release" of NDGA from the delivery systems of the present invention can easily be tested using methods that are known in the pharmaceutical arts. For example, the USP Dissolution Test Type 2 is commonly used to evaluate dissolution of drugs. Such an in vitro test is a well known surrogate for in vivo bioavailability and can easily be used to determine the pH at which the maximum level of NDGA is being released. (See, for example, J. Pharm Sci. 95 (7), Pages 1595-1605, 2006; Biopharmacuetucs & Drug Disposition 25: 91-98 (2004); and Pharmaceutical Research 12(3): 413-420 (1995).)

Digestive Tract

Our stomachs are vessels with 0.5-1.0 liter capacity. The contents of the stomach include hydrochloric acid, pepsinogen, and mucus. The pH of the stomach in a normal, healthy human is in the 1-4 range. There are many purposes for the high acidity found in the stomach. For example, high acidity is required to activate pepsinogen, which is the enzyme that initiates the digestion and breakdown of proteins that are ingested.

Gastric pH varies from time to time. Gastric acid is secreted in anticipation of a meal, to prepare for digestion. Gastric pH decreases as a result of acid secretion, and after a heavy meal, gastric pH correspondingly increases, and it also increases slightly in the blood, particularly in those segments of the circulatory system associated with supplying the gastrointestinal tract. This increase in blood pH is known as the "alkaline tide", and is caused by bicarbonate ions that are secreted into extracellular fluid of the stomach, then into venous blood.

Further down the alimentary canal is the small intestine, the first part of which is the duodenum. The pH of the duodenum is 5.0 to 5.5. The majority of nutrients, vitamins, and drugs are absorbed in this small area of the gastrointestinal tract. The pH in the middle portions of the intestinal tract (jejunum and ileum) ranges from 5.5 to about 6.5, while that in the lower part of the intestine (colon) ranges between 6.5 to 7.5. In addition to water, mucus, and electrolytes, secretions from the liver and pancreas join secretions from the intestinal mucosa to facilitate digestion and absorption of gastric contents. The anatomy of the small intestine is such that a very large surface area is available that provides better absorption of intestinal contents. The lining of the small intestines is composed of many villi, or finger like projections, which extend even more as projections called the brush border. The area is highly perfused with blood. These factors contribute to a very high surface area, increasing the likelihood of drug absorption taking place, if the ionization criterion is met.

Further along the small intestine, beyond the duodenum, lies the jejunum and ileum. Collectively, the small intestine has the highest surface area in the gastrointestinal system and the highest absorption of drugs occurs in the small intestine. In the lowest part of the intestine (rectum), the pH rises to about 7.5-8.0 and this area is not suitable for optimal absorption of some orally administered drugs like NDGA, which are acidic in nature; although some less acidic or more basic drugs are absorbed from the colon or rectal regions of the intestinal tract.

Formulation

The formulations of the present invention exhibit multimodal (e.g., bimodal, trimodal, etc.) release kinetics that incorporate sustained release systems. As used herein, in an exemplary embodiment, the delivery system is bimodal and is designed to deliver a portion of the dose (for example, >10% but <30%) to the stomach and part of the dose (for example, >30%) to the small intestines. This requires that at least a portion of the NDGA exhibits a release peak as tested in vitro at a pH of between 1 and 4, and another portion of the NDGA exhibits a release peak as tested in vitro at a pH of between 6.5 to 7.5. By "portion of the NDGA", this intends to mean the NDGA as found in the corresponding portion of the delivery system. For example, a first portion of the NDGA may be in a first portion of a tablet, such as the outer shell, and a second portion of the NDGA may be in a second portion of a tablet, such as the inner core. Such "apportioning" of the NDGA is described more fully below.

It is also a goal of this invention for essentially all (>90%) of the NDGA in a single oral dosage form to be delivered before passage of the NDGA into the large intestinal region, because NDGA is known to cause lesions in the cecum in animal toxicity studies. Accordingly, the formulations described herein usually include at least two different pH dependent delivery forms or vehicles combined into a single oral dosage form. For example, in the practice of the present invention, bimodal delivery systems are employed that allow selective delivery to both the stomach at a low pH (1 to 4), and the small intestines at a relatively neutral pH (6.5 to 7.5).

When this form of delivery system is used to deliver NDGA, there is the unexpected benefit that the early release form lowers the circulating triglyceride and free fatty acid (FFA) levels and the later release form affects glucose levels. This "one-two" punch affords a synergistic effect for enhancing the efficacy of NDGA on metabolic disorders and diabetes—by immediately lowering triglyceride and/or FFA levels, and high glucose levels can be more effectively replated or cleared during later release of NDGA. This pleiotropic pharmacological effect on fat and glucose metabolism is unique to NDGA in a multimodal delivery system.

In addition, by ensuring that the essentially all of the NDGA is administered prior to reaching the rectum, which would not be the case in a system relying solely on sustained release, one can avoid NDGA toxicity associated with it causing lesions in the cecum and rectum.

a. Multi-layer Tablets

In one embodiment, the delivery system comprises a multi-layer tablet, with the outside layer delivering the drug at a low pH (<4.0), whereas the inside layer or core keeps the drug from being released until the pH rises to 5.0 or above. See, for example, Journal of Controlled Release, 69(3): 455-466 (2000). In this example, the inside layer or core consists of an insoluble drug being trapped in a matrix of hydroxypropyl methylcellulose acetate succinate, which is insoluble at low pH values (such as in the stomach) and is water soluble at higher pH values (such as those seen in the intestinal tract). Due to the differences in polymer dissolution profiles, the drug release from such a matrix is time-dependent and the drug release is influenced by water transport, drug diffusion, polymer dissolution and pH of the dissolution medium. This approach has been applied to drugs such as acetaminophen and theophylline and it has been shown that the drug release is minimal in acidic pH (such as 0.1N HCl) and there is a significant increase in the release of the drugs in an increased pH environment (such as phosphate buffer at pH 7.4).

Most modified release oral dosage forms use hydrophilic polymer matrices to allow for a pH-regulated drug release profile. However, one disadvantage of the use of simple hydrophilic matrices is that the drug release profile is non-linear. A multi-layered matrix system overcomes the disadvantages associated with nonlinear release, by providing an additional release surface with time to compensate for the decreasing release rate, as the previous matrix release surface is diminishing. For example, such systems have been reviewed in J. Controlled Release 97(3): 393-405 (2004).

Multimodal release systems exhibiting controlled or sustained release characteristics can be obtained through the use of various hydrophilic polymer matrices and devices that can be used to include a matrix tablet, which is used as a core tablet for the preparation of multi-layer systems as well as other hybrid systems. Increasing the covered area of the core tablet results in a decrease in drug (NDGA) release and it modifies the dissolution rate of the drug. Other hybrid systems exhibit a pulsatile release feature (such as bi-modal or multi-modal), which offers significant advantages in therapies such as treatment of diabetes and metabolic disorders, through continuous regulation of high circulating glucose or triglyceride levels, following changes in the dietary states as well as daily circadian changes in these systems. For example, Eur Polymer J 42(5): 1183-1195 (2006) discusses the advantages of multi-layer or hybrid pulsatile release system formulations.

Enteric coatings can provide additional advantages of slow or sustained release profiles by allowing controlled release of drugs like NDGA through the pH-sensitive release in higher pH (such as that in the intestinal tract) through coating the core tablets with thin films. For example, polymeric coats can be constructed to create multi-layer films using polymers such as polyvinylpyrrolidone (PVP) and polymethacrylic acid (PMA), as described in Biomacromolecules 7(1): 27-30 (2006). Other materials used for coating include, for example, cellulose acetate phthalate, methyl acrylate-methacrylic acid copolymers, cellulose acetate succinate, hydroxyl propyl methyl cellulose phthalate, hydroxyl propyl methyl cellulose acetate succinate, polyvinyl acetate phthalate, methyl methacrylate-methacrylic acid copolymers, and sodium alginate/stearic acid copolymers.

b. Mixed Beads or Particles

Another approach to designing a bimodal delivery system is to put two types of pellets or beads containing the drug to be delivered in a single dissolvable capsule. For example, one type of bead may contain NDGA in a form that is immediately releasable in the stomach at low pH, while the second type of bead may contain NDGA in a form that is not releasable until it passes into the small intestines. See, for example, Biopharmaceutics and Drug Disposition, 25:91-98 (2004). As discussed above, this second type of bead may include an enteric coating to prevent the drug trapped in this type of bead from being absorbed in the stomach.

An approach, using polyelectrolyte complex (PEC) formations between materials such as pectin and chitosan, have been described to apply thin coats to acetaminophen to achieve bimodal drug release with increased pH, such as those seen in the colonic region of the intestine and can be used for NDGA (J Controlled Release 58(3): 303-310 (1999)).

NDGA loaded liposomal delivery systems with neutral or positive charges on the liposomes, dispersed in another matrix or gel can also provide bimodal or multimodal release profiles. Such an approach has been described for pH-sensitive ocular delivery for tropicanamide (Int J Pharm 190(1): 63-71 (1999)).

Pectin-based pellets produced by extrusion and spheronization process have been another technology applied to develop beads or particle-type sustained or modified release dosage forms allowing prolonged release profiles of NDGA. Granulation liquids such as ethanol allow the production of small, near spherical pellets and the type of granulation fluid is important for pectin molecules with high degree of free carboxylic acid residues. The use of microcrystalline cellulose in the matrix produces excellent control of size and shape and such technologies have been described in AAPS PharmSciTech 2(4): 54-62 (2001).

Water soluble drugs can be formulated in pectinate beads containing trimethyl chitosan chloride (TMC) as an absorption enhancer into novel bead and multi-particulate formulations that will allow modified and sustained release profile of drugs. Bead integrity through its transit in the gastrointestinal tract can be controlled through the use of techniques such as biomineralization of the beads or by coating the beads with high-methoxy-pectin (PHM) or Eudragit L30-D55 (Carbohydrate Polymers 61(1): 39-51 (2005).

c. Variably Degradable Polymer Matrices

Yet another approach to bimodal delivery is a system employing a composite matrix, with two different "scaffold" systems—one that allows release of NDGA at lower pH and one that does not. Such delivery systems often include the construction of complex polymerosomes or nanoparticles from both acid-labile and acid-stable polymeric scaffolds.

Biodegradable polymers such as polyhydroxyacids, polyanhydrides, polyorthoesters, polyaminoacids and polyphosphazenes have recently gained considerable interests due to their synthetic flexibility and versatility of applications. Controlled tuning of physicochemical properties of NDGA, including biodegradability is achieved through macromolecular substitutions. For example, the drug delivery applications of biodegradable polyphosphazenes are described in Adv Drug Delivery Rev 55(4): 467-482 (2003).

d. Drug Modifications and Conjugations

Bimodal drug delivery can also be achieved by using a first amount of a NDGA-polymer conjugate in conjuction with a second amount of nonconjugated NDGA or a second amount of a different NDGA-polymer conjugate, such that the different forms of NDGA exhibit bimodal delivery as described herein. For instance, polymerized collage fibers have been prepared to control the delivery of drugs. See, Biotechnol. Prog. 23(4): 990-994 (2007).

Polymeric drug delivery systems can not only improve solubility and release properties of the drugs, but can also be used for conjugation with drug substance to improve biodistribution and targeting of the drug to certain organs for delivery. An example of conjugating folic acid to the terminal amino groups of branched monofunctional and heterodifunctional polyethylene glycol (PEG) has been described in J Controlled Release 94(1): 39-51 (2004). A fullerene-paclitaxel conjugate has been synthesized as a slow-release drug candidate for aerosol liposomal delivery of paclitaxel for lung cancer therapy (J Am Chem Soc 127(36): 12508-12509 (2005)). This conjugated delivery system of paclitaxel is designed to release paclitaxel via enzymatic hydrolysis and a liposomal formulation of the conjugate in dilaurylphosphatidylcholine (DLPC) has shown excellent activity in lung cancer cells.

Uses a. Tumors and Cancers

NDGA is known to be useful in the treatment of a variety of different types of cancer. (See, for example, Breast Cancer Res. Treat., 94(1): 37-46 (2005).) Accordingly, the NDGA delivery systems of the present invention can be used to treat a variety of tumors and cancers. For example, the present invention can be used to treat various hematological malignancies such as lymphoblastic leukemia, myeloid leukemia, lymphocytic leukemia, childhood acute leukemia, chronic lymphocytic leukemia and hairy cell leukemia. Additional non-limiting examples may include malignant cutaneous T-cells, mycosis fungoides, non-malignant fibrous cutaneous T-cell lymphoma, lymphomatoid papulosis, T-cell rich cutaneous lymphoid hyperplasia, and Hodgkin's lymphoma.

Other various tumors and cancers that can be treated with the compounds and compositions of the present invention may also include bullous pemphigoid, discoid lupus erythematosus, lichen planus, adrenocortical carcinoma, Kaposi's sarcoma, bone cancer, neurological tumors and malignancies such as neuroblastoma, glioblastoma, astrocytoma, gliomas, brain tumor ependymoma, medulloblastoma, breast cancer, carcinoid tumor gastrointestinal, eye cancer, retinoblastoma, bladder cancer, carcinoma adrenocortical, carcinoma islet cell, clear cell cancer, colon cancer, esophageal cancer, intraocular melanoma, ductal cancer, dysplastic oral mucosa, gallbladder cancer, gastric (stomach) cancer, germ cell tumor, gestational trophoblastic tumor, hypopharyngeal cancer, intraocular melanoma, laryngeal cancer, and liver cancer.

It is further contemplated that the present invention may be used to treat lung tumors and cancers such as non-small cell lung cancer and small cell lung cancer, malignant mesothelioma, melanoma, merkel cell carcinoma, multiple endocrine neoplasia syndrome, mycosis fungoides, multiple myeloma, nasal cavity tumors, oropharyngeal cancer, parathyroid cancer, pheochromocytoma, pituitary tumor, pleuropulmonary blastoma, rectal cancer, rhabdomyosarcoma, sarcoma soft tissue adult, Sezary syndrome, skin cancer, thyroid cancer, urethral cancer, cervical cancer, ovarian tumors and cancer, uterine cancer, endometrial cancer, vaginal cancer, vulvar cancer, penile cancer, prostate cancer, Waldenstrom's macroglobulinemia, Wilms' tumor and tumors of the biliary duct.

a. Diabetes and Metabolic Disorders

NDGA has been investigated in a variety of rodent models and human subjects to evaluate its pharmacology and pharmacokinetics in diabetes and metabolic disorders. As used herein, "metabolic disorders" include hypertriglyceridemia, hyperglycemia, hyperinsulinemia, hyperlipidemia and high free fatty acid levels. Diabetes is a particular type of metabolic disorder. Diabetes mellitus, is often simply referred to as diabetes, and is a group of metabolic disorders in which a person has high blood sugar, either because they do not produce enough insulin (hypoinsulinemia) in Type 1 diabetes; or because they have an inefficient response to high levels of circulating insulin (hyperinsulinemia) as in Type 2 diabetes.

NDGA has been studied by administering it orally to animals to determine its effectiveness for lowering glucose, free fatty acid (FFA) and triglyceride levels. Glucose lowering effects of NDGA have been demonstrated and compared to metformin (a known diabetes treatment) in a non-diabetic rat model of hypertriglyceridemia (fructose-fed) and a non-genetic (fat-fed/STZ) rat model of non-insulin dependent diabetes mellitus (NIDDM), respectively. See Example 2 below. Treatment with equimolar doses of NDGA or metformin significantly lowered glucose in comparison to the vehicle control without any change in insulin concentrations. There was no significant baseline difference between the NDGA and metformin groups. These results demonstrate that both NDGA and metformin treatment effectively lower glucose concentration, and this effect is not appreciably different between the compounds when they are dosed on an equimolar basis.

Treatment with NDGA also dramatically and significantly lowered triglyceride concentrations by 80% in comparison to vehicle (or metformin). See Example 2 below. Metformin also significantly lowered triglycerides in comparison to the vehicle control in a less dramatic manner. Triglyceride concentrations in the NDGA-treated animals were significantly lower than those in the metformin-treated animals. Similar results were seen in plasma non-esterified fatty acids (free fatty acid (FFA)) and glycerol concentrations between NDGA, metformin and vehicle control. These results indicate that both compounds lower triglycerides and FFA levels, but that this effect is much greater with NDGA when both compounds are dosed on an equimolar basis. Accordingly, NDGA is superior at lowering glucose concentration and triglyceride concentration. In addition, it has been demonstrated that diabetes is not required for the triglyceride-lowering effect of NDGA.

Studies were also conducted to determine the mechanism by which NDGA lowers glucose. To do so, NDGA was administered to determine the effects of NDGA on insulin-stimulated glucose disposition and on basal hepatic glucose production using the high fat diet fed/streptozotocin (STZ) rat model of NIDDM. Whole-body insulin-stimulated glucose disposition was measured using a constant intravenous glucose/insulin infusion, in which the steady-state plasma insulin concentration (SSPI) is held constant and the steady-state plasma glucose concentration (SSPG) is a measure of net glucose clearance. NDGA treatment reduced the SSPG by approximately 30% (at steady state plasma insulin concentration) compared to that observed in the vehicle control group, suggesting that NDGA increases whole-body insulin sensitivity to increase plasma glucose clearance. In these same studies basal hepatic glucose production was measured using an intravenous infusion of radiolabeled glucose (no insulin was infused). NDGA treatment compared to vehicle significantly reduced hourly hepatic glucose production.

In the high fat diet-fed/STZ rat model, liver and muscle glycogen content was measured after treatment with NDGA versus vehicle. Treatment with NDGA had no effect on muscle glycogen levels when compared to control. Furthermore, NDGA reduced liver glycogen concentrations approximately 75%, suggesting that NDGA did not promote plasma glucose-lowering as a result of glycogen storage in these tissues. These results demonstrate that, at least in the high fat diet-fed/STZ rat model of non-insulin dependent diabetes mellitus (NIDDM), NDGA increases the whole-body insulin sensitivity and reduces hepatic glucose production.

It is likely that the triglyceride-lowering effect of NDGA may also be explained, at least in part, by the suppression of free fatty acid (FFA) release. Free fatty acids in the circulation can enter the liver and can be re-assembled into triglycerides by the process of re-esterification. By reducing the circulating concentrations of FFA, NDGA significantly reduces the substrate available for re-esterification and the subsequent secretion of triglycerides. Since NDGA treatment was demonstrated to inhibit liver triglyceride secretion, this likely represents the primary mechanism for the triglyceride-lowering effects of NDGA. It should be noted that other mechanisms for reducing triglycerides, such as increased triglyceride clearance, are not ruled out by these findings. In fact, triglyceride-lowering effects of NDGA at low doses of 10 and 20 mg/kg, in the hypertriglyceridemic rat model, occur at doses below which triglyceride secretion is affected.

These studies demonstrate that NDGA consistently lowers plasma glucose, triglyceride and free fatty acid levels in a variety of animal models of NIDDM and hypertriglyceridemia. In addition, NDGA increases whole-body insulin-stimulated glucose clearance and reduces basal hepatic glucose production. The effects of NDGA are not attributable to an increased insulin secretion, but it may reflect an insulin-like action on insulin sensitive tissue. Additionally, NDGA significantly lowers triglyceride concentrations by reducing liver triglyceride secretion.

EXAMPLES

Example 1

Models for NDGA Delivery

The multimodal characteristics of the delivery systems of the present invention can be evaluated using the single-pass intestinal perfusion method in a rat model, which exhibits a high correlation of rat permeability coefficient values when compared to humans. (International Journal of Durg Delivery 2 (2010): 69-75.)

The dissolution behavior and pH dependency of drug delivery systems can also be studied in vitro using known methods that are highly predictive of in vivo bioavailability. See, for example, Dissolution Technologies, May 2008, wherein the dissolution kinetics of azeclofenac, a low solubility lipophilic drug similar to NDGA was studied. The predictability of such in vitro dissolution tests and actual gastrointestinal permeability is well characterized. See, Pharmaceutical Research, 12(3) 413-420 (1994).

Accordingly, after formulation of a multimodal delivery system, the performance of such a delivery system in terms of delivery of NDGA over time and at different pHs can easily be determined using known methods.

Example 2

In Vivo NDGA Delivery Studies in Animals

The differences between immediate release and controlled release delivery systems for NDGA were studied, and the conclusion of these studies indicated that a multimodal delivery system including both early- and late-release forms of NDGA was particularly well suited for treatment of metabolic disorders and diabetes.

In these studies, a variety of rodent models were used to evaluate the glucose-lowering properties and its effects on lipids, such as lowering of triglycerides. NDGA was administered orally to animals over a wide range of doses (10 to 350) mg/kg.

Figure 2:
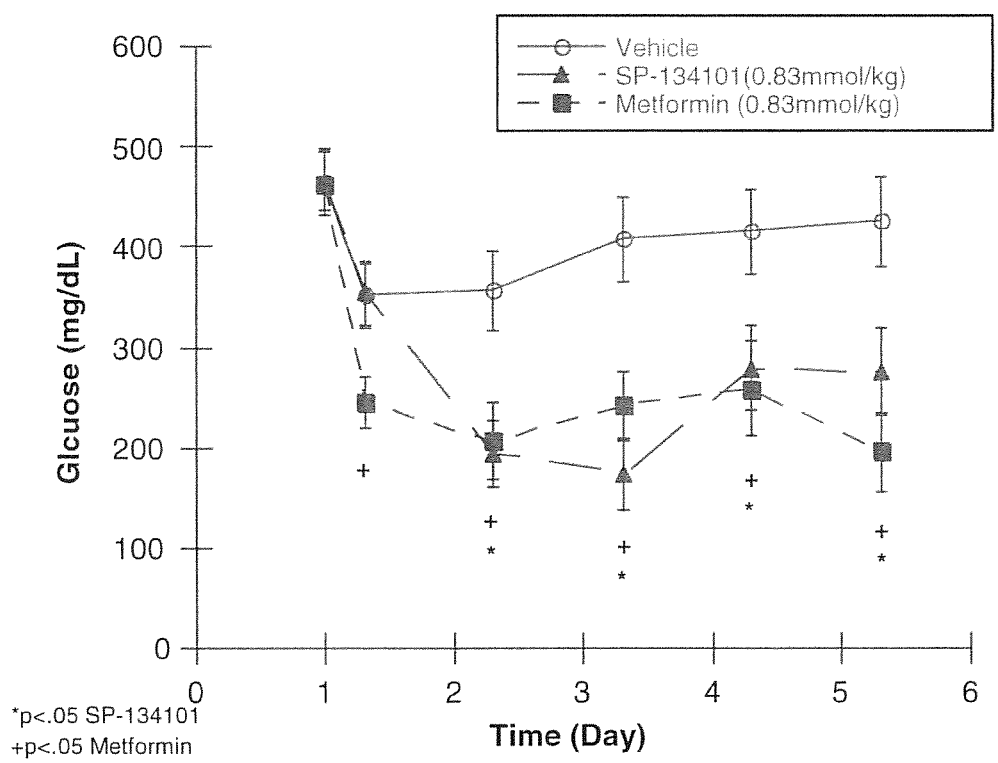
FIG. 2 shows the effects of metformin and NDGA on plasma glucose concentration over time as described in Example 2.
Figure 3:
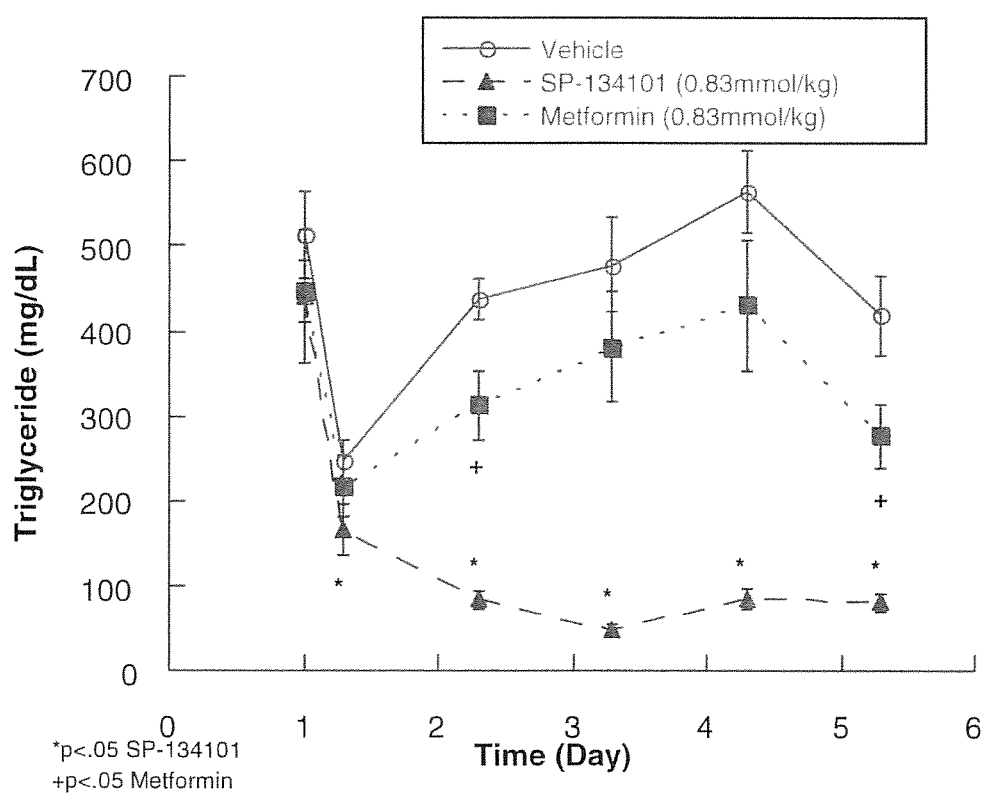
FIG. 3 shows the effects of metformin and NDGA on serum triglyceride concentration over time as described in Example 2.
Figure 4:
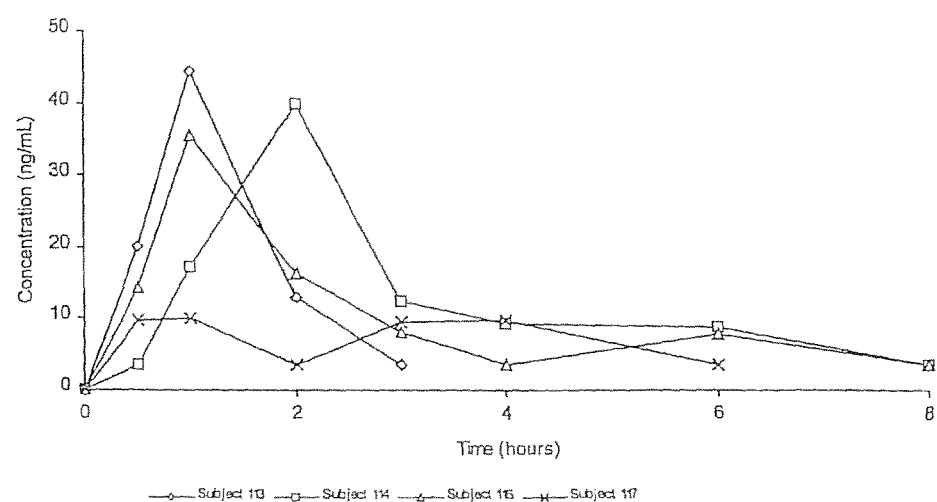
FIGS. 4 through 8 show the concentration vs. time curves at a dosage of 200 mg, 400 mg, 800 mg, 1600 mg and 2000 mg, respectively, as described in Example 3.
Figure 5:
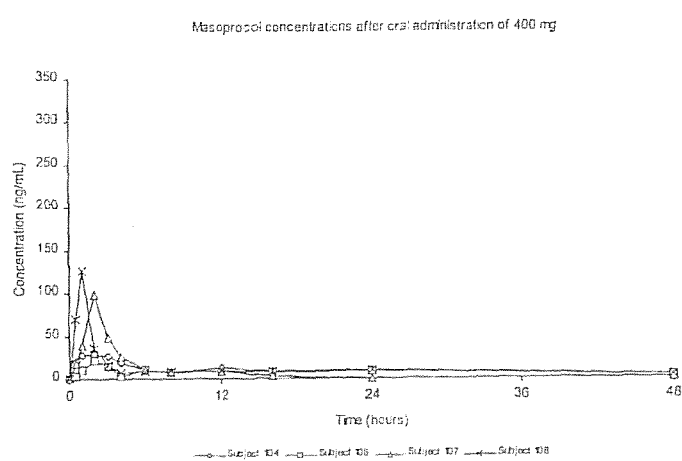
Figure 6:
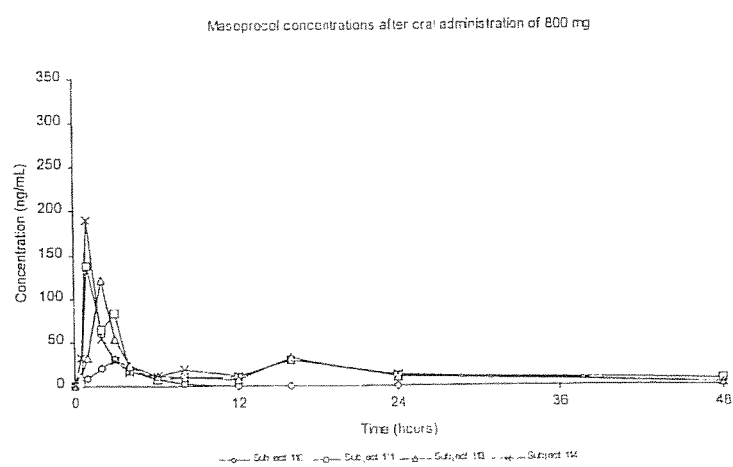
Figure 7:
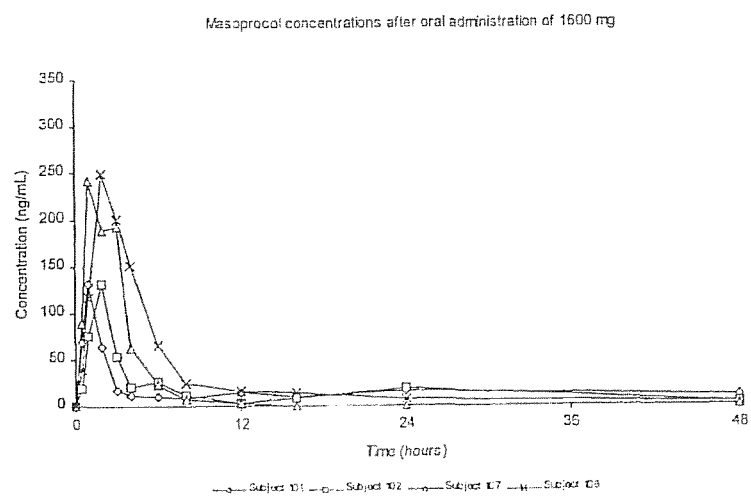
Figure 8:
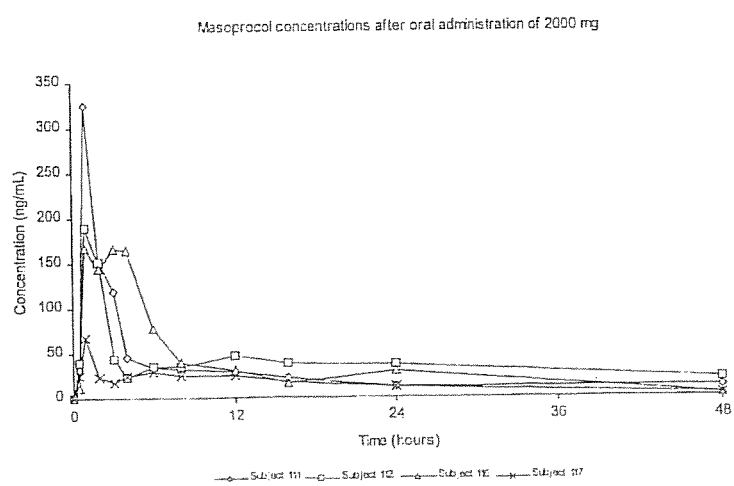

In one such study, the effects of NDGA and metformin as a control drug for treatment of diabetes were studied in a non-diabetic model of hypertriglyceridemia (fructose-fed) and a non-genetic, (i.e., streptozotocin (STZ) treated) model of diabetes. The results of this study demonstrated that both NDGA and metformin lowered glucose without changing insulin concentration, but that only NDGA significantly lowered triglycerides. See FIGS. 2 (glucose) and 3 (triglycerides).

In another more pertinent study, NDGA was dissolved in different delivery vehicles to demonstrate the effects of the delivery vehicle itself on the animal data. In this experiment, NDGA was dissolved in the following:

CMC: 0.25% carboxymethylcellulose

Gelucire: "Gelucire 44/14 (Gatefosse, Wildwood, N.J.; a well-defined mixture of mono-, di-, and tri-glycerides and mono- and di-fatty acid esters of polyethylene glycol)

PEG: 85% polyethylenene glycol, 10% tween and 5% propanediol

In this study, the following animal models where used:

Db/db mice: homozygous mice are a model of obesity, diabetes and dyslipedemia where their leptin receptor activity is deficient.

Ob/ob mice: obese mice with diabetes.

Db/lean mice: heterozygous mice that are not diabetic.

Fat/STZ rats: non-genetically diabetic overweight rats that are fed diets enriched in fat and made hyperglycemic by chemically removing their pancreatic function to reduce insulin production by treating them with streptozotocin (STZ).

Fructose/STZ rats: non-diabetic rats that are fed diets enriched in fructose and made hyperglycemic by treating them with STZ.

ZDF rats: obese and hyperglycemic rats with other metabolic disorders.

Baseline glucose and triglyceride concentrations, where appropriate, were measured for both diabetic and normal animals. These studies demonstrated that NDGA significantly lowers glucose when given orally to db/db and ob/ob mice with diabetes, as well as Fat/STZ rats and ZDF rats. In the mouse and rat models, a reliable glucose-lowering dose was achieved with NDGA at a dose of 150 mg/kg twice daily over a short dosing period, but the effect was more pronounced at higher doses of NDGA in the fat/STZ model.

NDGA was effective at lowering glucose when formulated in either aqueous or lipophilic vehicles to varying degrees of efficacy. Administration of NDGA once daily was generally ineffective at lowering glucose concentrations due to the short half-life of NDGA and a more consistent effect of lowering plasma glucose was seen with twice daily dosing of NDGA in various vehicles.

NDGA shows a dose- and time-dependence in its effects of lowering glucose since it was observed that a single daily dose of 150 mg/kg of NDGA was ineffective in lowering glucose in the fat/STZ rat and daily doses of 80 mg/kg twice daily did not lower glucose levels in the hypertensive fructose-fed rats. The in vitro studies of NDGA in adipocytes suggest that NDGA directly stimulates glucose transport to insulin-sensitive tissues and such a stimulation of glucose transport could explain its ability to lower glucose in diabetic rodent models. Furthermore, in vivo NDGA administration at the highest dose studied (350 mg/kg twice daily), did not result in increased insulin concentrations suggesting that NDGA lowers plasma glucose by an "insulin sensitizing" effect.

NDGA significantly and dramatically lowered plasma triglycerides in fat-fed/STZ, fructose-fed/STZ and ZDF rats. The demonstration of triglyceride lowering in the normoglycemic fructose-fed/hypertriglyceridemia rat model (fructose-fed/STZ) demonstrates that overt diabetes is not required for the triglyceride-lowering effect of NDGA and that NDGA acts through an "insulin sensitizing effect" for lowering plasma glucose levels, secondary to its ability to lower circulating triglyceride and free fatty acid levels, thus providing more "efficiency" to insulin in controlling glucose and fat regulation.

NDGA lowered triglyceride concentrations when formulated in either CMC, PEG or Gelucire vehicles, and at doses as low as 10 mg/kg twice per day. NDGA also lowered triglycerides when administered orally just once per day, a differentiated effect on triglyceride regulation when compared to glucose regulation, which required at a minimum, twice daily administration. The triglyceride-lowering efficacy of NDGA was significantly greater than that observed with metformin when both compounds were dosed on an equimolar basis.

NDGA shows an ability to lower plasma triglyceride levels in a variety of diabetic and non-diabetic animals to various degrees with different formulations and the effects appear to be dose- and/or time-dependent. These studies collectively demonstrate the beneficial effects of NDGA in lowering plasma glucose and triglyceride concentrations in animal models of NIDDM and hypertriglyceridemia.

Additional in vivo data have shown that NDGA also decreases free fatty acid (FFA) concentrations in different animal models: fat-fed/STZ and fructose-fed hypertriglyceridemic and fructose-fed/STZ rats. These reductions in free fatty acid concentration could result from either decreased production (by reduced lipolysis) or increased removal of free fatty acids from the circulation by liver, fat or muscle. The ability of NDGA to reduce glycerol (Gowri[a] et al., 1999, Reed et al., 1999), another product of triglyceride breakdown, suggests that NDGA inhibits adipose-tissue lipolysis, as shown in vitro by the inhibition of isoproterenol-induced lipolysis by NDGA in rat adipocytes (Gowri[a] et al., 1999).

Studies were conducted to determine the effects of NDGA (masoprocol) on insulin-stimulated glucose disposition and on basal hepatic glucose production using the fat/STZ rat. Whole-body insulin-stimulated glucose disposition was measured using a constant intravenous glucose/insulin infusion, in which the steady-state plasma insulin concentration (SSPI) is held constant and the steady-state plasma glucose concentration (SSPG) is a measure of net glucose clearance. Masoprocol treatment reduced the SSPG 30% from that in the vehicle control group ($p<0.05$) suggesting that masoprocol (NDGA) acts through increasing whole-body insulin sensitivity—a novel and unique pharmacological effect. Furthermore, NDGA (masoprocol) treatment significantly reduced hourly hepatic glucose production ($p<0.05$).

The triglyceride-lowering effect of NDGA may be explained by the suppression of free fatty acid (FFA) release. Free fatty acids in the circulation can enter the liver and be re-assembled into triglycerides in a process known as re-esterification. By reducing the concentrations of circulating FFA, NDGA significantly reduces the substrate available for re-esterification and subsequent secretion as triglycerides. Since NDGA treatment was demonstrated to inhibit liver triglyceride secretion, this likely represents the primary mechanism for the triglyceride-lowering effects of masoprocol (NDGA) and provides a unique and novel dose- and time-dependent effect of NDGA on regulation of: first, triglyceride and FFA levels, and second, glucose transport in an "insulin-sensitizing" manner (rather than increasing insulin release). NDGA (masoprocol) does not promote glucose lowering as glycogen storage in these tissues. The results of these studies collectively demonstrate that, in the fat/STZ rat model of NIDDM, NDGA (masoprocol) increases whole-body insulin sensitivity and reduces hepatic glucose production.

In conclusion, various in vitro and in vivo studies demonstrate that NDGA consistently lowers glucose, triglyceride and free fatty acid levels in a variety of animal models of NIDDM, hyperglycemia and hypertriglyceridemia. In addition, NDGA increases whole-body insulin-stimulated glucose disposal and reduces basal hepatic glucose production. The effects of NDGA are not attributable to an increase in insulin secretion, and may well reflect an insulin-like action on insulin sensitive tissue. Additionally, NDGA dramatically lowers triglyceride concentrations by reducing liver triglyceride secretion.

In summary, the results described above indicated that by modifying the release characteristics of NDGA, through administration as an oral suspension in CMC, PEG or Gelucire, each having a different affect on the NDGA release profile, one achieves a different pharmacological benefit on lowering triglyceride, free fatty acid and/or glucose levels. For example, in the Fat/STZ rat model, using the same daily dosage of NDGA (40 mg/Kg once daily (QD)), there is no significant lowering of triglyceride levels using NDGA (327 mg/dl +/−25 without NDGA and 270+/−26 with NDGA in the CMC delivery vehicle, whereas there is a significant lowering of triglyceride levels using NDGA (674+/−84 without NDGA and 312+/−38 with NDGA) in the Gelucire delivery vehicle. In another example in the same Fat/STZ rat diabetes model, using the NDGA twice daily dosing at 250 mg/kg, there is no significant lowering of glucose levels using NDGA (393+/−20 without NDGA and 364+/−20 with NDGA) in the PEG delivery vehicle, whereas there is a significant lowering of glucose levels using NDGA in a Gelucire vehicle (497+/−22 without NDGA and 380+/−28 with NDGA).

In addition, the above results have demonstrated that a multimodal delivery system can be useful in achieving a "dose sparing" effect. For example, in the Fat/STZ rat model, there was essentially no difference in glucose or triglyceride level lowering effect of NDGA; when NDGA was given orally at a dose of 40 mg QD or 250 mg/kg QD in a Gelucire vehicle. For glucose, the effects were 366+/−32 versus 299+/−25 mg/dl at 40 mg/kg QD and 366+/−32 versus 325+/−26 mg/dl at 250 mg/kg QD NDGA. Furthermore, the effects on triglyceride lowering at 40 mg/kg QD were 674+/−84 versus 312+/−38 mg/dL and at 250 mg/kg QD, the triglyceride lowering effects were 674+/−84 versus 249+/−42, indicating a minimal difference between the two doses in the Gelucire vehicle on the pharmacological effects on lowering glucose or triglyceride levels. Accordingly, if NDGA in Gelucire had been combined with NDGA in a second delivery vehicle, "dose sparing" effects could have been achieved and less overall NDGA would have been administered to the patient to achieve the same pharmacological result; thus limiting the adverse effects associated with a potential higher dose of NDGA.

Furthermore, the differential results described above are evidence of differential release profiles between one delivery vehicle and the other. Accordingly, one can achieve, through modifying the absorption of NDGA by utilizing a multimodal delivery system, a better safety profile and avoid the toxicity of NDGA, for example, to the cecal region of the large intestine.

Example 3

In Vivo NDGA Clinical Studies in Humans

The first Phase I study of NDGA was an ascending-dose, single-dose, single-blind (subject), placebo-controlled study conducted in healthy male volunteers between 18 and 45 years old. Fourteen subjects participated in up to 3 study periods, and 5 doses of NDGA were studied: 200, 400, 800, 1600, and 2000 mg. During each study period the subjects were monitored for safety for 72 hours following NDGA oral administration. Blood samples collected following NDGA administration were used to determine NDGA concentrations in plasma. The study was carried through to completion, with each tested dose (200, 400, 800, 1600, and 2000 mg) being considered safe. The orally administered NDGA used in the study was contained in white, opaque, size 3 gelatin capsules. Each capsule contained 100 mg of NDGA.

The results for each of the five doses are depicted in FIGS. 4 to 8 corresponding to 200, 400, 800, 1600 and 2000 mg dosages, respectively. As shown, at all five doses, the concentration vs. time curves are unimodal (single peak).

The pharmacokinetic parameters of NDGA as observed in this experiment are given below in Table 1:

TABLE 1

Pharmacokinetic Parameters of NDGA

| Parameter | Dose | | | | |
|---|---|---|---|---|---|
| | 200 mg | 400 mg | 800 mg | 1600 mg | 2000 mg |
| $C_{max}$ (ng-eq/ml) | 32.6 +/− 15.3 | 69.1 +/− 51.6 | 120.3 +/− 66.3 | 189.3 +/− 65.7 | 187.6 +/− 106.0 |
| $T_{max}$ (hr) | 1.3 +/− 0.5 | 1.8 +/− 0.5 | 1.8 +/− 1.0 | 1.5 +/− 0.6 | 1.0 +/− 0.0 |
| $AUC_{0-last}$ (ng-eq hr/ml) | 66 +/− 26 | 385 +/− 90 | 591 +/− 252 | 889 +/− 252 | 1380 +/− 514 |

Table 1 demonstrates that the pharmacokinetic profile of NDGA following oral administration in a capsule (immediate release) formulation provides a "unimodal peak" concentration with a rapid elimination of NDGA at lower dose levels. Furthermore, as depicted in FIGS. 4 to 8, increasing dose levels of NDGA resulted in less than dose proportional "unimodal peaks" and did not provide a another "dose release" opportunity in the intestinal segments. These data illustrate the beneficial properties of a multimodal release oral dosage form of NDGA.

The second Phase I study of NDGA was an open-label, randomized, two-period crossover study designed to determine if a high-fat meal affects the absorption of NDGA, and to provide preliminary information about possible gender differences in the pharmacokinetics of NDGA. A total of 16 healthy volunteers (8 men and 8 women), ranging in age from 19 to 48 years old, participated in this study. Each subject received an active NDGA dose under fasted conditions and another under fed conditions (the two study periods were separated by a 7-day washout period). Blood samples were collected immediately before and for 48 hours following NDGA administration and used for determination of plasma concentrations of NDGA. The NDGA used in the study was provided in white, opaque Size 0 gelatin capsules. Each capsule contained 250 mg of NDGA.

The results of the safety study of NDGA are shown below in Table 2:

TABLE 2

Summary of Patients Reporting Adverse Events

| Body System | Event | Placebo (n = 12) | Masoprocol (n = 29) |
| --- | --- | --- | --- |
| Body as a whole | Abdominal pain | 1 | 1 |
| | Asthenia | 0 | 2 |
| | Headache | 2 | 8 |
| | Neck rigidity | 0 | 1 |
| | Pain | 0 | 1 |
| Cardiovascular system | Syncope | 0 | 1 |
| Digestive system | Diarrhea | 0 | 2 |
| | Dyspepsia | 0 | 1 |
| | GI hemorrhage | 0 | 1 |
| | Increased appetite | 0 | 1 |
| | Vomiting | 0 | 1 |
| Nervous system | Dizziness | 1 | 1 |
| | Hyperesthesia | 0 | 1 |
| Respiratory system | Increased coughing | 1 | 1 |
| | Pharyngitis | 1 | 1 |
| Special senses | Eye pain | 0 | 1 |
| Urogenital system | Hematuria | 0 | 1 |

The examples set forth above are provided to give those of ordinary skill in the art with a complete disclosure and description of how to make and use the preferred embodiments of the compositions, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for treating a metabolic disorder in a subject comprising oral administration of a nordihydroguiaretic acid (NDGA) composition to the subject, wherein the NDGA composition is comprised in a multi-modal drug delivery system defined by multi-modal NDGA delivery kinetics, and wherein the multi-modal drug delivery system comprises:

a first portion of the NDGA composition that is releasable at a peak pH of 1 to 4, and a second portion of the NDGA composition that is a releasable at a peak pH of 5.0 to 7.5, wherein over 30% of a total portion of NDGA present in the NDGA composition is present in the second portion, and over 90% of the total portion of NDGA present in the NDGA composition is releasable at a pH of 7.5 or lower, and wherein the structure of the NDGA comprised in the first portion or the second portion of the single dose of NDGA is given by Formula I:

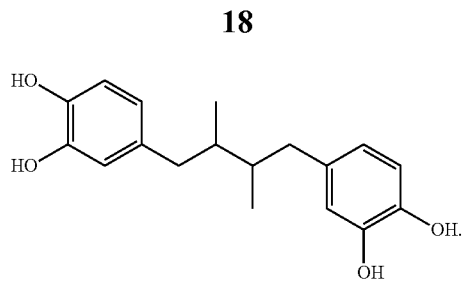

2. A method for treating a metabolic disorder in a subject comprising oral administration of a nordihydroguiaretic acid (NDGA) composition to the subject, wherein the NDGA composition is comprised in a multi-modal drug delivery system defined by multi-modal NDGA delivery kinetics, and wherein the multi-modal drug delivery system comprises:

a first portion of the NDGA composition that is releasable at a peak pH of 1 to 4, and a second portion of the NDGA composition that is releasable at a peak pH of 5.0 to 7.5, wherein over 10% of a total portion of NDGA present in the NDGA composition is present in the first portion, over 30% of the total portion of NDGA present in the NDGA composition is present in the second portion, and over 90% of the total portion of NDGA present in the NDGA composition is releasable at a pH of 7.5 or lower, and wherein the structure of the NDGA comprised in the first portion or the second portion of the single dose of NDGA is given by Formula I:

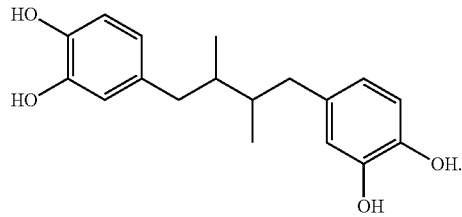 [SMILES: CC(Cc1ccc(O)c(O)c1)C(C)Cc1ccc(O)c(O)c1]

3. The method according to claim 1, wherein over 10% but less than 30% of the total portion of NDGA present in the NDGA composition is present in the first portion.

4. The method according to claim 2, wherein the multi-modal NDGA delivery kinetics comprises a bimodal absorption kinetic profile.

5. The method according to claim 1, wherein the metabolic disorder is manifested by high free fatty acids, hyperlipidemia, hyperglycemia or hyperinsulinemia.

6. The method according to claim 5, wherein the metabolic disorder is diabetes.

7. The method according to claim 6, wherein the diabetes is non-insulin dependent diabetes mellitus (NIDDM).

8. The method according to claim 1, wherein the multi-modal drug delivery system comprises a multi-layer tablet to control the release of the first portion and the second portion.

9. The method according to claim 1, wherein the multi-modal drug delivery system comprises mixed beads or particles to control the release of the first portion and the second portion.

10. The method according to claim 1, wherein the multi-modal drug delivery system comprises polymers to control the release of the first portion and the second portion.

11. The method according to claim 10, wherein the polymers comprise a variably degradable polymer matrices.

12. The method according to claim 1, wherein the multimodal drug delivery system comprises a drug modification or conjugation.

13. The method according to claim 1, wherein the multimodal NDGA delivery kinetics comprise a bimodal absorption kinetic profile.

14. The method according to claim 1, further comprising administering the NDGA composition once a day.

15. The method according to claim 1, further comprising administering the NDGA composition twice a day.

16. The method according to claim 1, wherein the NDGA composition contains between 200 to 2000 milligrams of NDGA.

* * * * *